United States Patent [19]
Clarke et al.

[11] Patent Number: 5,969,173
[45] Date of Patent: Oct. 19, 1999

[54] METHOD OF MAKING DIALKALI METAL SILANOLATES AND SILOXANOLATES

[75] Inventors: Stephen Ross Clarke, Morphett Vale, Australia; Daniel Graiver, Midland, Mich.; Janis Gunars Matisons, Marion, Australia; Michael James Owen, Midland, Mich.

[73] Assignee: Dow Corning Corporation, Midland, Mich.

[21] Appl. No.: 09/203,317

[22] Filed: Dec. 1, 1998

[51] Int. Cl.⁶ ........................................................ C02F 7/08
[52] U.S. Cl. .............................................. 556/459; 556/450
[58] Field of Search ..................................... 556/459, 450

[56] References Cited

U.S. PATENT DOCUMENTS

| | | | |
|---|---|---|---|
| 5,629,401 | 5/1997 | Graiver | 528/43 |
| 5,637,668 | 6/1997 | Gravier | 528/33 |
| 5,856,546 | 1/1999 | Graiver | 556/459 |

*Primary Examiner*—Paul F. Shaver
*Attorney, Agent, or Firm*—James L. De Cesare

[57] ABSTRACT

Dialkali metal organosilanolate and dialkali metal organosiloxanolate salts are manufactured from cyclic siloxanes or linear silicone polymers using a heterogeneous interfacial reaction process. A stoichiometric excess of an alkali metal hydroxide such as potassium hydroxide or an alkali metal oxide as a solid or dissolved or dispersed in a compatible solvent, is prepared and used as a first phase. The cyclic siloxane or linear silicone polymer is placed in a second phase either dissolved or dispersed in another solvent which is immiscible with the first phase. The resulting silanolate and siloxanolate salts can be used as monomers for solid-liquid phase and liquid-liquid phase interfacial polymerization or in a polycondensation process for the synthesis of alternating siloxane polymers. They can also be used as ring opening initiators for the base catalyzed polymerization of cyclic siloxanes.

17 Claims, No Drawings

METHOD OF MAKING DIALKALI METAL SILANOLATES AND SILOXANOLATES

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A MICROFICHE APPENDIX

Not applicable.

FIELD OF THE INVENTION

This invention is directed to a method for preparing dialkali metal organosilanolate and dialkali metal organosiloxanolate salts using a heterogeneous interfacial reaction technique.

BACKGROUND OF THE INVENTION

Alkali metal organosilanolates and alkali metal organosiloxanolates can be used as initiators for base catalyzed ring opening polymerization of cyclic siloxanes to produce high molecular weight siloxane polymers. Primarily, potassium trimethylsilanolate is used to ring open cyclic trisiloxanes, cyclic tetrasiloxanes, and cyclic pentasiloxanes. Lithium organosilanolate salts have also been used to ring open cyclic trisiloxanes and cyclic tetrasiloxanes for the production of a narrow molecular weight distribution of siloxane polymers.

Another use for alkali metal organosilanolates and alkali metal organosiloxanolates is in the synthesis of siloxane bonds using a condensation type reaction. A generalized reaction scheme for such a process is shown below:

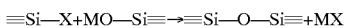

where M is a Group IA metal such as Na or K, and X is halogen. Thus, when M is Na and X is Cl, for example, the reaction is:

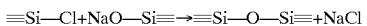

Such silanolates and siloxanolates can be obtained by the reaction of diorganoalkoxysilanes with alkali metal hydroxides, or by the reaction of diorganosilanols with alkali metals or alkali metal hydroxides. These methods and their details can be found, for example, in British Patent 631,506 (Nov. 3, 1949), and in U.S. Pat. No. 3,641,090 (Feb. 8, 1972). Mono-alkali metal organosilanolates have also been produced by cleavage of the siloxane bond from the corresponding hexaorganodisiloxane compound, using an alkali metal hydroxide dissolved in an alcoholic solution. This procedure was reported by Hyde in U.S. Pat. No. 2,472,799 (Nov. 25, 1946); by Hyde, Johannson, Daudt, Fleming, Laudenslager and Roche in J. Amer. Chem. Soc. (75) 1953, 5615; and by Tatkock and Rochow in J. Amer. Chem. Soc. (72), 1950, 528. The synthesis of sodium triorganosilanolate using such a procedure is shown below:

U.S. Pat. No. 5,629,401 (May 13, 1997) and U.S. Pat. No. 5,637,668 (June 10, 1997) describe the synthesis of solvent soluble dipotassium organosiloxanolates. This was achieved by the equilibration reaction of cyclic siloxanes such as octamethylcyclotetrasiloxane or tetramethyltetraphenylcyclotetrasiloxane dissolved in cyclohexane solvent, with an aqueous solution of potassium hydroxide, where water was continuously removed by a distillation process. It is noted in the '401 and '668 patents that the synthesis of relatively short-chain sizes of soluble dipotassium organosiloxanolate polymers with a chain length of three siloxane units is also possible. Lithium hydroxide aqueous solutions were also used in the '401 and '668 patents for the preparation of dilithium organosiloxanolates by a similar procedure.

In contrast, and with respect to the present invention, a heterogeneous interfacial reaction is used to produce dialkali metal organosilanolate and dialkali metal organosiloxanolate salts. According to this method, a stoichiometric excess of an alkali metal hydroxide or an alkali metal oxide is used in a first phase, while a cyclic or linear siloxane polymer is used in a second phase. The first and second phases are immiscible with each other, so that the reaction occurs at the interface of the two phases, to produce a product which is then isolated using an extraction procedure.

The advantage of this present technique is that it can be tailored such that the product separates as a fine gel or as a suspension in a selected solvent, while excess unreacted alkali metal hydroxide and/or unreacted alkali metal oxide settles to the bottom of the reaction vessel. Isolation of the resulting silanolate or siloxanolate is a simple procedure in which the liquid gel is decanted, leaving residual alkali metal hydroxide and/or alkali metal oxide. Preferably, this is followed by solvent washing of unreacted alkali metal hydroxide and/or alkali metal oxide, and addition of the washings to the decanted gel. If desired, the gel can then be filtered to remove the suspended silanolate or siloxanolate, rewashed with a low boiling point solvent, re-filtered, and dried to obtain a final product.

However, because the dialkali metal organosilanolate or dialkali metal organosiloxanolate salt produced by this present procedure is a progressive degradation of a cyclic or linear polysiloxane reagent, it is necessary to ensure that the correct degree of degradation has occurred. In this regard, dialkali metal organosilanolates and dialkali metal organosiloxanolates formed by the process are alkaline dibasic salts which are readily soluble in water. Thus, they hydrolyze to produce two mole of hydroxy ions for each mole of salt. The $OH^-$ ions can be titrated with standardized hydrochloric acid to determine the alkali content. The titration yields information about the salt such as (i) alkali metal ion content, (ii) the $K_b$ or $pK_b$ of the salt, and (iii) the average number of silicon atoms in the dialkali metal organosilanolate or dialkali metal organosiloxanolate salt, i.e., the chain length of the salt.

In one preferred embodiment according to this invention, dipotassium dimethylsilanolate and dipotassium dimethylsiloxanolate are prepared by a heterogeneous reaction between solid, insoluble KOH, and a polysiloxane dissolved in toluene. The reaction is believed to occur by virtue of an initial cleavage of the siloxane bond by the hydroxy ion, to form a potassium silanolate group and a silanol group. The silanol group is then converted to a second potassium silanolate because of the presence of excess KOH.

This reaction scheme is shown below:

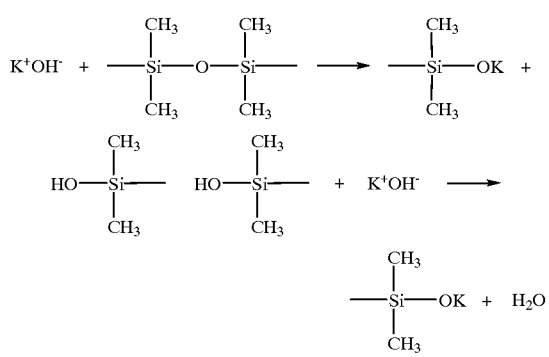

The reaction occurs progressively until the product separates out of solution as an insoluble dipotassium salt. Cyclic polysiloxanes used in the reaction degrade to single dipotassium dimethylsilanolates after about a 48 hour reaction period. Shorter reaction times lead to blends of dipotassium dimethylsilanolate and dipotassium dimethylsiloxanolate containing two silicon atoms. Linear siloxane polymers used in the reaction yield dipotassium dimethylsiloxanolates with 2–4 silicon atoms. Fourier transform infrared analysis of the reaction mix reveals that the rate of polysiloxane concentration reduction in the toluene solution is more rapid and more complete for the linear siloxane polymers than for the cyclic polysiloxanes. It is postulated that this occurs because linear siloxane polymers can more readily migrate onto the KOH surface than cyclic polysiloxanes.

BRIEF SUMMARY OF THE INVENTION

This invention is related to dialkali metal organosilanolate and dialkali metal organosiloxanolate salts, and to a method of making dialkali metal organosilanolate and dialkali metal organosiloxanolate salts, using an heterogeneous interfacial reaction.

Dialkali metal organosilanolates and dialkali metal organosiloxanolates manufactured according to this method can be represented by the formula $MO(R''R'SiO)_nM$ where R' and R'' are alkyl radicals containing 1–6 carbon atoms, aryl radicals, alkenyl radicals, or alkylamino radicals. M in the formula represents an alkali metal in Group IA of the Periodic Table, i.e., lithium, sodium, potassium, rubidium, cesium, and francium. Most preferred alkali metals are sodium and potassium. In the formula, "n" represents an integer with a value of at least one or more. Thus, "n" has a value of 1 for dialkali metal organosilanolates, and "n" has a value of greater than 1 for dialkali metal organosiloxanolates.

In the process, a linear siloxane polymer or a cyclic polysiloxane are employed as one of the reactants. One type of suitable linear siloxane polymer generally corresponds to the formula $XO(R''R'SiO)_nX'$ where R' and R'' represent alkyl radicals of 1–6 carbon atoms, aryl radicals, alkenyl radicals, or alkylamino radicals. X and X' represent terminal end groups on the polymer such as alkyl radicals of 1–6 carbon atoms, aryl radicals, alkenyl radicals, or X and X' can be hydrogen. The value of n is preferably 3 or more.

Another type of suitable linear siloxane polymer generally corresponds to the formula $X(R''R'SiO)_{n'}SiR'R''X'$ where R' and R'' represent alkyl radicals of 1–6 carbon atoms, aryl radicals, alkenyl radicals, or alkylamino radicals. X and X' represent terminal end groups on the polymer such as alkyl radicals of 1–6 carbon atoms, aryl radicals, alkenyl radicals, or X and X' can be hydrogen. The value of n' is preferably 1 or more.

Cyclic polysiloxanes used in the process can be represented by the formula $(R''R'SiO)_n$ where R' and R'' represent alkyl radicals of 1–6 carbon atoms, aryl radicals, alkenyl radicals, or alkylamino radicals. The value of n in the case of the cyclic polysiloxane should be from 3 to about 6.

These and other features of the invention are explained and become apparent from a consideration of the following detailed description thereof.

BRIEF DESCRIPTION OF THE SEVERAL VIEWS OF THE DRAWING

Not applicable.

DETAILED DESCRIPTION OF THE INVENTION

According to the present invention, a heterogeneous interfacial reaction is used to produce a dialkali metal organosilanolate or a dialkali metal organosiloxanolate salt. A stoichiometric excess of an alkali metal hydroxide MOH such as potassium hydroxide, or an alkali metal oxide $M_2O$, are used in the preparation of a first phase. The alkali metal hydroxide and the alkali metal oxide can be used in their solid form, or they can be dissolved or dispersed in a compatible solvent.

A linear siloxane polymer or a cyclic polysiloxane are used to prepare a second phase for the heterogeneous interfacial reaction. The linear siloxane polymer and the cyclic polysiloxane may be used "neat", or they may be dissolved or dispersed in a compatible solvent.

In any event, it is necessary that the first phase and the second phase be immiscible with each other. The reaction occurs at the interface of the two phases, and the products can be isolated using an extraction procedure.

One representative product which can be manufactured according to this procedure is the well-defined dipotassium dimethylsilanolate salt shown below:

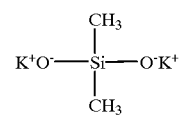

Another representative product which can be manufactured according to this procedure is a dialkali metal organosiloxanolate, such as a dipotassium dimethylsiloxanolate salt corresponding to the formula shown below in which n is 1 or more, preferably 1 to about 8.

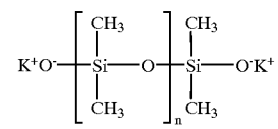

There are a number of optional procedures which can be used in carrying out the method according to this invention. In one embodiment of the method, for example, (i) a solid insoluble alkali metal hydroxide or a solid insoluble alkali metal oxide, can be dispersed in a linear siloxane polymer or in a cyclic polysiloxane which are dissolved in an appropriate solvent, such that the solution containing the siloxane is immiscible with the solid insoluble alkali metal hydroxide or the solid insoluble alkali metal oxide. In a second embodiment of the method, (ii) a solid insoluble alkali metal hydroxide or a solid insoluble alkali metal oxide can be dispersed in a "neat" linear siloxane polymer or in a "neat" cyclic polysiloxane, without any solvents. In a third embodiment of the method, (iii) an alkali metal hydroxide or an alkali metal oxide can be dissolved or dispersed in an appropriate solvent, and then reacted with a "neat" linear siloxane polymer or with a "neat" cyclic polysiloxane, such that the linear siloxane polymer or the cyclic polysiloxane are insoluble in the solution containing the alkali metal hydroxide or in the solution containing the alkali metal oxide. In a fourth embodiment of the method, (iv) an alkali metal hydroxide or an alkali metal oxide can be dissolved or dispersed in an appropriate solvent, and then reacted with a linear siloxane polymer or with a cyclic polysiloxane which are also dissolved in a suitable solvent, such that the solution containing the linear siloxane polymer or the solution containing the cyclic polysiloxane is immiscible with the solution containing the alkali metal hydroxide or the solution containing the alkali metal oxide. In the fourth embodiment, the two solutions must be immiscible in each other so that a reaction can occur heterogeneously across the two phases.

While any of the four representative methods (i), (ii), (iii), or (iv), can be used to produce dialkali metal organosilanolates and dialkali metal organosiloxanolates according to this invention, method (i) is most preferred because of the ease with which a product from the method can be isolated. However, according to method (ii), the product may form in the linear siloxane polymer or in the cyclic polysiloxane, i.e., the polysiloxane, or it may disperse or dissolve into the polysiloxane, thereby requiring a more complex extraction procedure. In method (iii), the product may preferentially dissolve into the alkali metal hydroxide solution, which would also require a more complex extraction procedure. Finally, in method (iv), the product may dissolve into one of the liquid phases, again requiring a complex extraction procedure.

When method (i) is used to prepare a dialkali metal organosilanolate or a dialkali metal organosiloxanolate, then in that case, a solid flake or a pelletized technical or reagent grade of KOH is the most preferred alkali metal hydroxide for use according to that particular embodiment. The solvent which is used to dissolve the polysiloxane, however, must be so selected as not to dissolve the alkali metal hydroxide, i.e., KOH, or the reaction product, i.e., the dialkali metal organosilanolate or the dialkali metal organosiloxanolate. The solvent must also be selected such that that it is one that is not capable of undergoing any undesired side reactions with any starting material or with any resulting product.

Anhydrous toluene is the most preferred solvent for this particular embodiment, because dialkali metal organosilanolates and dialkali metal organosiloxanolates are caused to separate as a fine powder, which is suspended in the solvent, eventually forming a gel. The gel can be then be readily separated from any unreacted alkali metal hydroxide, i.e., KOH, by simple decanting.

Other materials suitable for use as the solvent, other than toluene, include alkanes such as butane, pentane, hexane, heptane, octane, nonane, and pentane; aromatic solvents such as benzene and xylenes; chlorinated solvents such as carbon tetrachloride, chloroform, dichloromethane, chloromethane, 1,1,1-trichloroethane, and 1,1,2-trichloroethane; linear and cyclic ethers such as diethyl ether and tetrahydrofuran; ketones such as acetone, methyl ethyl ketone and methyl isobutyl ketone; esters such as ethyl acetate, propyl acetate, and butyl acetate; and miscellaneous solvent materials such as dimethyl sulfoxide or acetonitrile.

In carrying out the process, the choice of using a linear siloxane polymer or a cyclic polysiloxane will determine whether one obtains a dialkali metal organosilanolate or a dialkali metal organosiloxanolate. Generally, linear siloxane polymers $XO(R"R'SiO)_nX'$ where n is greater than or equal to 3, and linear siloxane polymers $X(R"R'SiO)_nSiR'R"X'$ where n' is greater than or equal to 1, result in the formation of dialkali metal organosiloxanolates. On the other hand, cyclic polysiloxanes $(R"R'SiO)_n$ where n is 3, 4, 5, or 6, are more likely to produce dialkali metal organosilanolates. However, given appropriate reaction conditions, it is possible to prepare dialkali metal organosiloxanolates from cyclic polysiloxanes.

A preferred procedure for carrying out the method according to the invention basically involves selecting and placing a solvent in a reaction vessel, and dissolving a linear siloxane polymer or a cyclic polysiloxane in the selected solvent. The reaction should be carried out in a manner such that the temperature of the contents in the reaction vessel can be carefully controlled. An alkali metal hydroxide or an alkali metal oxide is then added to the reaction vessel, and the contents of the reaction vessel are continuously stirred. Stirring of the contents of the reaction vessel is continued until the reaction is complete. A continuous blanket of dry nitrogen or other inert dry gas such as argon, is generally used to fill the reaction vessel in the space above the reactants, in order to prevent the ingress of moisture into the vessel.

Dialkali metal organosilanolate and dialkali metal organosiloxanolate salts are produced as fine powders as a result of this procedure. However, depending on the organic solvent selected, the final product may take the form of a semi-translucent or semi-liquid gel. For example, anhydrous toluene is an example of a solvent which not only does not interfere with the reaction process, but a solvent which provides for the formation of well structured gels.

During the procedure, unreacted and excess alkali metal hydroxide or alkali metal oxide will settle to the bottom of the reaction vessel, and this can be easily separated from the product by decanting the gel. The remaining part of the product left in the reaction vessel is removed by several washings with dry toluene. Care should be taken to ensure that none of the alkali metal hydroxide or the alkali metal oxide is collected along with these toluene washings. If desired, toluene washings are added to the decanted gel.

When the gel is vacuum filtered under a dry nitrogen or argon atmosphere, it leaves a pancake-like semi-solid. The pancake-like semi-solid is redispersed in anhydrous hexane by stirring to remove residual toluene, and then it can be vacuum filtered.

At all times, the process generally should be carried out in a dry atmosphere. Thus, all preparative work could be conducted at a work station filled with a dry inert gas such as nitrogen or argon. Where this procedure is not possible, preparative work could be conducted under a dry inert gaseous atmosphere such as a nitrogen gas blanket. Vacuum Atmosphere work stations filled with a dry argon atmosphere are suitable for these purposes. Since the product is readily formed as an hygroscopic powder, it generally should be stored immediately under an inert nitrogen or argon blanket. In particular, for example, it can be stored in a sealed glass jar filled with nitrogen gas, and then placed in a Vacuum Atmosphere workstation under an argon atmosphere, prior to re-opening the jar for testing of the product. Preferably, moisture in such workstations should be controlled to a level less than about 50 ppm.

Since the type of polysiloxane used as the starting material influences the type of product obtained, testing of the final product is generally necessary to ensure that the correct type of product has been obtained, and some suitable testing procedures are detailed below. As previously noted, linear siloxane polymers result in the formation of dialkali metal organosiloxanolates, while cyclic polysiloxanes are more likely to produce dialkali metal organosilanolates. In addition, the reaction is also of a progressive degradative nature, with the result that generally higher reaction temperatures and longer reaction times tend to form dialkali metal organosilanolates and/or short-chain dialkali metal organosiloxanolates, whereas lower temperatures and shorter reaction times generally tend toward the formation of longer-chain dialkali metal organosiloxanolates.

It is also generally necessary to confirm that the correct degree of degradation has occurred. In this regard, it should be noted that dialkali metal organosilanolates and dialkali metal organosiloxanolates are difunctional, hydrolyzable, alkaline dibasic salts which are readily soluble in water. Thus, they hydrolyze to produce two mole of hydroxy ions for each mole of the salt. The $OH^-$ ions can be titrated with standardized hydrochloric acid in order to determine the amount of alkali released on hydrolysis. Such a titration will yield considerable information about the salt such as:

a) the alkali metal ion content of the salt,
b) the $pK_b$ of the salt, and
c) the average number of silicon atoms in the dialkali metal organosilanolate or in the dialkali metal organosiloxanolate salt, i.e., the chain length of the salt.

Thus, the hydrolysis of a dialkali metal organosilanolate or a dialkali metal organosiloxanolate salt can be described as depicted below in the reaction scheme.

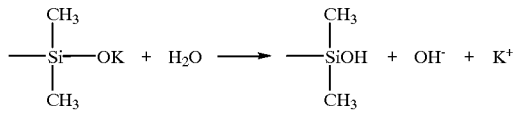

The basicity of such products can be determined, for example, by standard acid/base titrations, calculated using relationships such as those shown below:

$K_b = [\text{silanediol}][OH^-]^2/[\text{silanolate}]$ where $[OH^-] = 10^{-(14-pH)}$, [silanediol]=$[OH^-]/2$, and [silanolate]=[0.16×titre (ml)/2×100]−[silanediol].

A typical titration procedure involves using a sample mass of about 0.45 gram of the product being tested, dissolved in 100 ml of deionized water, and directly titrated with 0.1600M HCl solution. The pH can be continuously monitored using a calibrated pH meter, in order to determine the end point of the titration. The end point is taken as the maximum rate of change of pH with respect to titre volume. Normally, this occurs at a pH of about 8 to 9. The $[OH^-]$ concentration in the equation shown above can then be determined from the initial pH of the aqueous sample solution, and this will generally range from 12 to about 12.85 depending upon the product type being tested.

The average number of silicon atoms in the product can be estimated from the results of this acid/base titration using equations such as the two shown below. In these equations, the sample mass relates to the mass of material dissolved in deionized water for the titration, i.e., 0.45 g, that is titrated with the 0.1600M aqueous HCl solution.

Average Number of Silicon atoms=m×Y+(1−Y)×(m+1)
Y=0.1600×titre (ml)×(94+74 m)/2×1000 mass (gm)

In order to estimate the average number of silicon atoms in a silanolate or siloxanolate molecule using these equations, it is necessary to calculate the mole fraction 'Y' of silanolate or siloxanolate having 'm' silicon atoms in the molecule. For this purpose, whole number integer values of 'm' can be used which increase in value, such that highest value of 'm' is chosen when the calculated result for 'Y' obtained from the second equation is the closest value to one, but not exceeding one. The value 'Y' is therefore the mole fraction of silanolate/siloxanolate species of molecular weight (94+74 m), and '1−Y' is the mole fraction of silanolate/siloxanolate species of molecular weight (164+74 m).

It should be noted that these equations relate only to products such as dipotassium silanolate and dipotassium siloxanolate which are made from linear polydimethylsiloxane polymers and dimethylcyclosiloxanes. Equations for products prepared using other types of siloxane polymers and other types of alkali metal hydroxides would of necessity have to be modified accordingly.

For purposes of illustration, four dipotassium dimethylsiloxanolates and one dipotassium dimethylsilanolate compounds were prepared according to the method of this invention, and were analyzed by acid base titration using the techniques explained above. The results are shown in Table I

TABLE I

| Compound | Initial pH | $K_b$ | $pK_b$ | Average Si Atoms |
|---|---|---|---|---|
| 1 | 12.13 | 1.73 × 10$^{-4}$ | 3.8 | 3.3 |
| 1 (repeat) | 12.05 | 0.85 × 10$^{-4}$ | 4.1 | 3.2 |
| 2 | 12.54 | 45.7 × 10$^{-4}$ | 2.3 | 1.7 |
| 3 | 12.05 | 0.81 × 10$^{-4}$ | 4.1 | 3.0 |
| 4 | 12.53 | 24.9 × 10$^{-4}$ | 2.6 | 1.5 |
| 5 | 12.85 | dissociates | — | — |

These results were plotted as $K_b^{-1}$ versus the average number of silicon atoms per molecule, and it was found that as the length of the siloxanolate chain grows, that the basicity of the dipotassium siloxanolate salt decreases.

When these types of dipotassium dimethylsilanolate and dipotassium dimethylsiloxanolate salts are treated with a slight excess of a strong acid such as concentrated hydrochloric acid, polydimethylsiloxane fluids are produced. The fluids when analyzed by FT-IR (Fourier transform infrared spectroscopy) have typical aliphatic absorptions at 2958 cm$^{-1}$ and 2898 cm$^{-1}$; distinct silicon-methyl absorption at 1260 cm$^{-1}$; characteristic polymeric siloxane broad double peaks at 1092 cm$^{-1}$ and 1011 cm$^{-1}$; and finally silicon-dimethyl absorption at 798 cm$^{-1}$.

Based on titration data explained previously, it is believed that such polymerization proceeds by a two step process. In the first step, dimethyldihydroxysilane is formed from dipotassium dimethylsilanolate; and an alpha-omega, dihydroxy dimethylsiloxane is formed from dipotassium dimethylsiloxanolate salt at the neutralization point, that is a pH of 8 to 9. A slight excess of the acid will protonate the silanol functional groups, producing an acid catalyzed polymerization, and this is consistent with the concept described by Lasocki and Chrzczonowicz in the Journal of Polymer Science, Volume 59, Page 259, (1962), where a mechanism for the acid catalyzed step-growth polymerization of silanediols was proposed as depicted below:

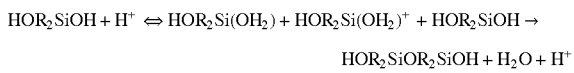

EXAMPLES

The following examples are set forth for the purpose of illustrating the present invention in more detail.

Example I

This example relates to the preparation of dipotassium dimethylsilanolate salt using a heterogeneous interfacial reaction technique. The reaction was carried out in a Pyrex 500 ml, three-neck, round-bottom flask, to which was added 150.05 grams of toluene. The toluene was distilled, and then dried over anhydrous sodium sulfate prior to use. Octamethylcyclotetrasiloxane (10.126 gram) was added to the reaction vessel. This material constituted 96% octamethylcyclotetrasiloxane and 4% decamethylcyclopentasiloxane. A Teflon stirrer blade connected to a glass stirring shaft was used to continuously agitate the mix with slow to medium speed stirring. The stirring shaft was placed through the center neck of the round-bottom flask to which was fitted a Teflon bearing with about an 0.5 mm clearance from the stirring shaft. A flameproof motor was connected to the stirrer shaft and used to turn the stirrer blade. A dry nitrogen feed was fitted to one of the two side-neck openings of the reaction vessel. Nitrogen gas was slowly fed with a slight positive pressure into the reaction vessel to provide an inert gaseous blanket over the reaction mix. The nitrogen was allowed to escape through the bearing to ensure that there was no ingress of moisture. The temperature of the reaction mix was controlled to 40° C.±3° C. by placing the reaction vessel into a temperature controlled silicone oil bath. A Teflon coated thermocouple was fed directly into the reaction mix though the other opening of the reaction vessel. This opening was maintained air-tight once it was placed into position. The thermocouple was used to turn the heat source for the silicone oil bath on and off and to maintain the desired temperature of the reaction mix. The mix was then allowed to equilibrate to 40° C.±3° C. Once equilibrated, 39.94 gram of potassium hydroxide in flake form was added to the reaction mix through one of the two side necks on the reaction vessel. The nitrogen gas feed and the thermocouple were replaced into position, and the mix was continuously stirred at 40° C.±3° C. for 48 hours. The dipotassium organosilanolate salt was produced as a fine powder. It formed a semi-translucent, semi-liquid gel since anhydrous toluene was used as the solvent. The unreacted excess potassium hydroxide settled to the bottom of the reaction vessel and was easily separated from the product by decanting the gel. Residual product in the flask was removed by several careful washings with dry toluene. Care was taken to ensure that no potassium hydroxide was collected with the toluene washings. The toluene washings were then added to the decanted gel. The gel was vacuum filtered under dry nitrogen, leaving a pancake-like, semi-solid. This pancake-like semi-solid was redispersed in anhydrous hexane with stirring to remove residual toluene, and then vacuum filtered. At all times the work was carried out in a dry nitrogen gas blanket. The dry product readily formed a white powder, and was immediately stored under an inert nitrogen blanket as the product was hygroscopic. The product was stored in a sealed glass jar, filled with nitrogen gas, and placed in a Vacuum Atmosphere workstation under an argon atmosphere prior to re-opening the jar for testing of the product. Moisture in the workstation was controlled to less than about 50 ppm.

The product was tested to confirm that the correct material had been obtained. Thus, an aqueous solution of the product (0.4502 gram dissolved in 100.0 ml of deionized water) was titrated with standardized 0.1600M hydrochloric acid in order to determine the $K_b$ of the salt and the average number of silicon atoms of the salt. The $K_b$ was found to be infinitely large, indicating that the salt had fully dissociated in water. The Average number of silicon atoms=[mass (g)×2×1000] divided by [168×0.1600×titre (ml)]=0.954. The experimental yield was 5.221 gram which was 22.7% of the theoretical yield.

Example II

This example relates to the preparation of dipotassium dimethylsiloxanolate salt using a solid-liquid phase heterogeneous interfacial reaction technique. Example I was repeated except that 150.9 gram of toluene was used instead of 150.05 gram of toluene, 9.74 gram of a polydimethylsiloxane fluid having a viscosity of 350 centipoise (mPa·s) was used instead of 10.126 gram of octamethylcyclotetrasiloxane, 23.35 gram of potassium hydroxide was used instead of 39.94 gram of potassium hydroxide, and stirring of the mix was continued for 24 hours instead of 48 hours.

As in Example I, this product was tested using an aqueous solution of the product (0.4301 gram dissolved in 100.0 ml of deionized water), which was titrated with standardized 0.1600M hydrochloric acid to determine the $K_b$ of the salt and the average number of silicon atoms of the salt. The $K_b$ was found to be $8.1 \times 10^{-5}$. The Average number of silicon atoms was calculated as 2.20. The mole fraction of dipotassium tetramethyldisiloxanolate was calculated at 80.39%, and the mole fraction of dipotassium hexamethyltrisiloxanolate was calculated at 19.61%. The experimental yield was 15.20 gram, which was 45.0% of the theoretical yield using 2.20 as the average number of silicon atoms in the product. This analysis indicated a carbon content of 20.3% and a hydrogen content of 5.1%.

Example III

The product from Example II was heated at a steadily increasing temperature and decomposed via a condensation reaction. This resulted in a series of volatile cyclic siloxane polymers being released. $K_2O$ was eliminated as the small molecule during this condensation reaction. This surprising discovery was made by heating 2.502 mg of the product from Example II at a rate of 10° C./minute, from room temperature to about 600° C., and continuously measuring the sample weight. A TA Instruments Company 2200 thermogravimetric analyzer was used to carry out this experiment. A nitrogen gas blanket was applied over the sample at a flow rate of 50 mm/minute, to prevent oxidative degradation. The results obtained in this example are shown in Table 2. The Table indicates that the decomposition temperatures used in this example can be directly correlated to literature boiling points, for the resulting series of cyclic polydimethylsiloxanes, which had 3–7 siloxane repeat units. RES in this Table indicates the Residue.

TABLE 2

| Wt. Loss | Amt. % | Temp. Range °C. | Peak °C. | Compound | Boiling Point °C. |
|---|---|---|---|---|---|
| 1st | 1.37 | 30–80 | 73 | Organics | — |
| 2nd | 10.74 | 80–120 | 100 | Water | 100.0 |
| 3rd | 3.91 | 120–155 | 136 | Hexamethylcyclotrisiloxane | 135.1 |
| 4th | 4.90 | 155–180 | 164 | Octamethylcyclotetrasiloxane | 175.4 |
| 5th | ~2 | 180–220 | 210 | Decamethylcyclopentasiloxane | 211.0 |
| 6th | ~3 | 220–260 | 227 | Cyclic D6 | 245.0 |
| 7th | 6.39 | 260–315 | 284 | Cyclic D7 | 275.6 |
| RES | 67.53 | >315 | >315 | Polymeric Dimethylsiloxane | — |

A reaction scheme accounting for this surprising thermal degradation of the dipotassium dimethylsiloxanolate salt is shown below:

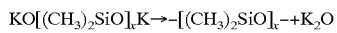

$$KO[(CH_3)_2SiO]_kK \rightarrow [(CH_3)_2SiO]_k + K_2O$$

Other variations may be made in compounds, compositions, and methods described herein without departing from the essential features of the invention. The embodiments of the invention specifically illustrated herein are exemplary only and not intended as limitations on their scope except as defined in the appended claims.

We claim:

1. A method of making a dialkali metal organosilanolate or a dialkali metal organosiloxanolate comprising the steps of
   (A) interfacially reacting (i) a stoichiometric excess of an alkali metal hydroxide or an alkali metal oxide as a first phase, with (ii) a cyclic polysiloxane or a linear siloxane polymer as a second phase; at or near an interface formed by the first phase and the second phase, the first phase and the second phase being immiscible one with the other, so that reaction occurs at the interface of the first phase and the second phase; and
   (B) recovering a dialkali metal organosilanolate or a dialkali metal organosiloxanolate at or near the interface of the first phase and the second phase.

2. A method according to claim 1 in which the dialkali metal organosilanolate and the dialkali metal organosiloxanolate have the formula $MO(R''R'SiO)_nM$ where R' and R" represent alkyl radicals containing 1–6 carbon atoms, aryl radicals, alkenyl radicals, or alkylamino radicals; M is an alkali metal in Group IA of the Periodic Table; and n represents an integer with a value of at least one.

3. A method according to claim 1 in which the cyclic polysiloxane has the formula $(R''R'SiO)_n$ where R' and R" represent alkyl radicals of 1–6 carbon atoms, aryl radicals, alkenyl radicals, or alkylamino radicals, and n is 3–6.

4. A method according to claim 1 in which the linear siloxane polymer has the formula $XO(R''R'SiO)_nX'$ or the linear siloxane polymer has the formula $X(R''R'SiO)_nSiR'R''X'$ where R' and R" represent alkyl radicals of 1–6 carbon atoms, aryl radicals, alkenyl radicals, or alkylamino radicals; X and X' represent alkyl radicals of 1–6 carbon atoms, aryl radicals, alkenyl radicals, or hydrogen; n is at least 3; and n' is at least one.

5. A method according to claim 1 in which the alkali metal hydroxide and the alkali metal oxide contain an alkali metal in Group IA of the Periodic Table.

6. A method according to claim 1 in which the first phase comprises a solid insoluble alkali metal hydroxide or a solid insoluble alkali metal oxide, and the second phase comprises a linear siloxane polymer or a cyclic polysiloxane dissolved in a solvent to form a solution, so that the solution containing the linear siloxane polymer or the solution containing the cyclic polysiloxane is immiscible with the solid insoluble alkali metal hydroxide or the solid insoluble alkali metal oxide.

7. A method according to claim 1 in which the first phase comprises a solid insoluble alkali metal hydroxide or a solid insoluble alkali metal oxide, and the second phase comprises a neat linear siloxane polymer or in a neat cyclic polysiloxane, without a solvent in either phase.

8. A method according to claim 1 in which the first phase comprises an alkali metal hydroxide or an alkali metal oxide dissolved in a solvent to form a solution, and the second phase comprises a neat linear siloxane polymer or a neat cyclic polysiloxane, so that the neat linear siloxane polymer or the neat cyclic polysiloxane are insoluble in the solution containing the alkali metal hydroxide or in the solution containing the alkali metal oxide.

9. A method according to claim 1 in which the first phase comprises an alkali metal hydroxide or an alkali metal oxide dissolved in a solvent to form a solution, and the second phase comprises a linear siloxane polymer or a cyclic polysiloxane dissolved in a solvent to form a solution, so that the solution containing the linear siloxane polymer or the solution containing the cyclic polysiloxane is immiscible with the solution containing the alkali metal hydroxide or the solution containing the alkali metal oxide.

10. A method according to claim 6 in which the solvent is selected from the group consisting of toluene, butane, pentane, hexane, heptane, octane, nonane, pentane, benzene, xylenes, carbon tetrachloride, chloroform, dichloromethane, chloromethane, 1,1,1-trichloroethane, 1,1,2-trichloroethane, diethyl ether, tetrahydrofuran, acetone, methyl ethyl ketone, methyl isobutyl ketone, ethyl acetate, propyl acetate, butyl acetate, dimethyl sulfoxide, and acetonitrile.

11. A method according to claim 8 in which the solvent is selected from the group consisting of toluene, butane, pentane, hexane, heptane, octane, nonane, pentane, benzene, xylenes, carbon tetrachloride, chloroform, dichloromethane, chloromethane, 1,1,1-trichloroethane, 1,1,2-trichloroethane, diethyl ether, tetrahydrofuran, acetone, methyl ethyl ketone, methyl isobutyl ketone, ethyl acetate, propyl acetate, butyl acetate, dimethyl sulfoxide, and acetonitrile.

12. A method according to claim 9 in which the solvent is selected from the group consisting of toluene, butane, pentane, hexane, heptane, octane, nonane, pentane, benzene, xylenes, carbon tetrachloride, chloroform, dichloromethane, chloromethane, 1,1,1-trichloroethane, 1,1,2-trichloroethane, diethyl ether, tetrahydrofuran, acetone, methyl ethyl ketone, methyl isobutyl ketone, ethyl acetate, propyl acetate, butyl acetate, dimethyl sulfoxide, and acetonitrile.

13. A method according to claim 9 in which the dialkali metal organosilanolate or the dialkali metal organosiloxanolate is heated at a steadily increasing temperature and decomposed until there is formed a plurality of cyclic polydimethylsiloxanes having from 3 to 7 siloxane repeating units.

14. A method according to claim 13 in which the dialkali metal organosilanolate or the dialkali metal organosiloxanolate are heated at a rate of 10° C./minute from room temperature to about 600° C.

15. A method according to claim 1 in which the dialkali metal organosilanolate is dipotassium dimethylsilanolate of the formula $KO[(CH_3)_2SiOK$.

16. A method according to claim 1 in which the dialkali metal organosiloxanolate is dipotassium dimethylsiloxanolate of the formula $KO[(CH_3)_2SiO]_nK$ where n is 2–8.

17. A method for making a dialkali metal-containing organosilicon compound comprising:

(A) reacting two immiscible phases at or near the interface formed by said phases, wherein the first phase comprises a stoichiometric excess of an alkali metal hydroxide or an alkali metal oxide, and wherein the second phase comprises a cyclic polysiloxane or a linear siloxane polymer; and (B) recovering the dialkali metal containing organosilicon compound.

* * * * *